(12) United States Patent
Freeman et al.

(10) Patent No.: US 11,679,019 B2
(45) Date of Patent: Jun. 20, 2023

(54) PORTABLE URINE CONTAINER

(71) Applicants: Az Freeman, Waverly, GA (US); Angelia Freeman, Waverly, GA (US)

(72) Inventors: Az Freeman, Waverly, GA (US); Angelia Freeman, Waverly, GA (US)

( * ) Notice: Subject to any disclaimer, the term of this patent is extended or adjusted under 35 U.S.C. 154(b) by 312 days.

(21) Appl. No.: 17/196,279

(22) Filed: Mar. 9, 2021

(65) Prior Publication Data
US 2022/0287866 A1 Sep. 15, 2022

(51) Int. Cl.
*A61F 5/441* (2006.01)
*A61F 5/453* (2006.01)
*A61F 5/455* (2006.01)

(52) U.S. Cl.
CPC .............. *A61F 5/441* (2013.01); *A61F 5/453* (2013.01); *A61F 5/4556* (2013.01)

(58) Field of Classification Search
CPC ....................................................... A61F 5/441
USPC ........... 4/144.1–2, 449, 1; 600/573; 604/327
See application file for complete search history.

(56) References Cited

U.S. PATENT DOCUMENTS

| | | | | |
|---|---|---|---|---|
| 5,331,689 A | * | 7/1994 | Haq | A47K 11/12 604/326 |
| 5,411,496 A | * | 5/1995 | Homa | A61F 5/441 424/408 |
| 5,797,147 A | * | 8/1998 | Young | A61G 9/006 604/350 |
| 6,588,024 B2 | | 7/2003 | Koelliker | |
| 6,968,577 B1 | * | 11/2005 | Taft, Jr. | A47K 11/12 604/350 |
| 7,846,143 B1 | | 12/2010 | Abbato | |
| 8,650,669 B1 | * | 2/2014 | Kolter | A47K 11/12 4/144.1 |
| D780,308 S | | 2/2017 | Hovermale | |
| 9,603,471 B2 | * | 3/2017 | Green | B65D 47/06 |
| 9,603,737 B2 | * | 3/2017 | Jenkin | A47K 11/12 |
| 2007/0136936 A1 | * | 6/2007 | Malloy | A47K 11/12 4/144.1 |
| 2008/0163411 A1 | | 7/2008 | Brown | |
| 2012/0174303 A1 | * | 7/2012 | Escobar | A61F 5/4556 4/144.1 |
| 2014/0310859 A1 | * | 10/2014 | Brown | A61G 9/006 4/144.1 |
| 2016/0364814 A1 | * | 12/2016 | Yekutiely | G06F 16/9535 |
| 2017/0020317 A1 | * | 1/2017 | Green | A47G 19/2272 |
| 2020/0337484 A1 | * | 10/2020 | Sorensen | A47J 43/27 |
| 2023/0074503 A1 | * | 3/2023 | Kanellos | B01F 35/3204 |

FOREIGN PATENT DOCUMENTS

| | | | | |
|---|---|---|---|---|
| DE | 60020397 T2 | * | 11/2005 | ............. A61F 5/441 |
| WO | WO-2018106871 A1 | * | 6/2018 | ............. A61F 5/441 |
| WO | WO-2019156709 A1 | * | 8/2019 | ......... A47G 19/2272 |
| WO | WO-2021092624 A1 | * | 5/2021 | ......... A47G 19/2205 |

* cited by examiner

*Primary Examiner* — Lori L Baker
(74) *Attorney, Agent, or Firm* — Lawrence J. Gibney, Jr.

(57) ABSTRACT

A portable male urinal will allow the long haul truckdriver or others engaged in long road trips to relieve themselves when facilities are not otherwise readily available. A handle is provided on a sealed container with a flared opening in the opening of the container is large enough to receive the urine. A tapered insert, which forms part of the flared opening which will allow the user to empty the contents without spilling the contents during disposal.

4 Claims, 4 Drawing Sheets

PORTABLE URINE CONTAINER

BACKGROUND OF THE INVENTION

A. Field of the Invention

This relates to containers and specifically portable urine containers that may be used by truck drivers on a long distance trip. The truck driver, for instance, must be able to relieve himself or herself on the road while at the same time insuring that the contents do not spill during transit. This device addresses those concerns.

B. Prior Art

There are many other prior art references that describe portable urine containers. A representative example of this type of device can be found at Abbato U.S. Pat. No. 7,846,143, which teaches a vessel with a funnel shaped opening and a valve that will open upon the deposit of the fluid and will prevent the spillage of urine during normal use. In order to empty the contents the person must handle the opening by unscrewing the funnel shaped device and emptying the container.

Another reference can be found at Brown U.S. Patent publication 2008/0163411. This device is a specific system for truck drivers but is substantially different than the current application.

Another reference is Taft, U.S. Pat. No. 6,968,577. The Taft reference is comprised of a handle with an internal valve that can be opened and locked in place by the user. Once the urine is deposited the user closes the internal valve to seal the urine in the container.

There are other references in the prior art that teach portable urine collection systems but none teach the use of a specially designed tapered insert with an opening on the side of the insert.

BRIEF SUMMARY OF THE INVENTION

Truckdrivers or anyone who must make long distance travel sometimes find the need to void the body of urine. This may be difficult on very long trips and sometimes impractical. Truck drivers are usually paid by the mile so it is important for the driver to maintain the operation of the vehicle as much as possible. This device will allow the elimination of urine from the person with a minimum of down time. Another related challenge to collecting the urine is to make sure that the urine does not spill from the container into which it has been deposited especially when the vehicle is moving.

This container allows the driver to collect and store the urine is a spill-proof vessel that can be stored in the cab of the truck until the contents can be emptied. A deodorizer may also be added to address the smell issue that is commonly found with stored urine. The device will be comprised of a vessel with an integrated handle. A lid will be provided on the opening on the top of the container. A tapered opening will extend downward and inward into the container. On the side of this opening will be a cutout through which the urine can be emptied at the arrival of the destination.

The specially formed insert can be either made as part of the container or be inserted into the opening by internal threads on the top of the container or made as part of the vessel. With this device the user does not touch the top of the container when the device is emptied, and it is intended that the insert is not removed.

The contents of the container are emptied by unscrewing the lid of the device and simply pouring out the contents through the opening that is proved on the insert in the top of the vessel.

NUMBERING DESCRIPTION

Figure 1:
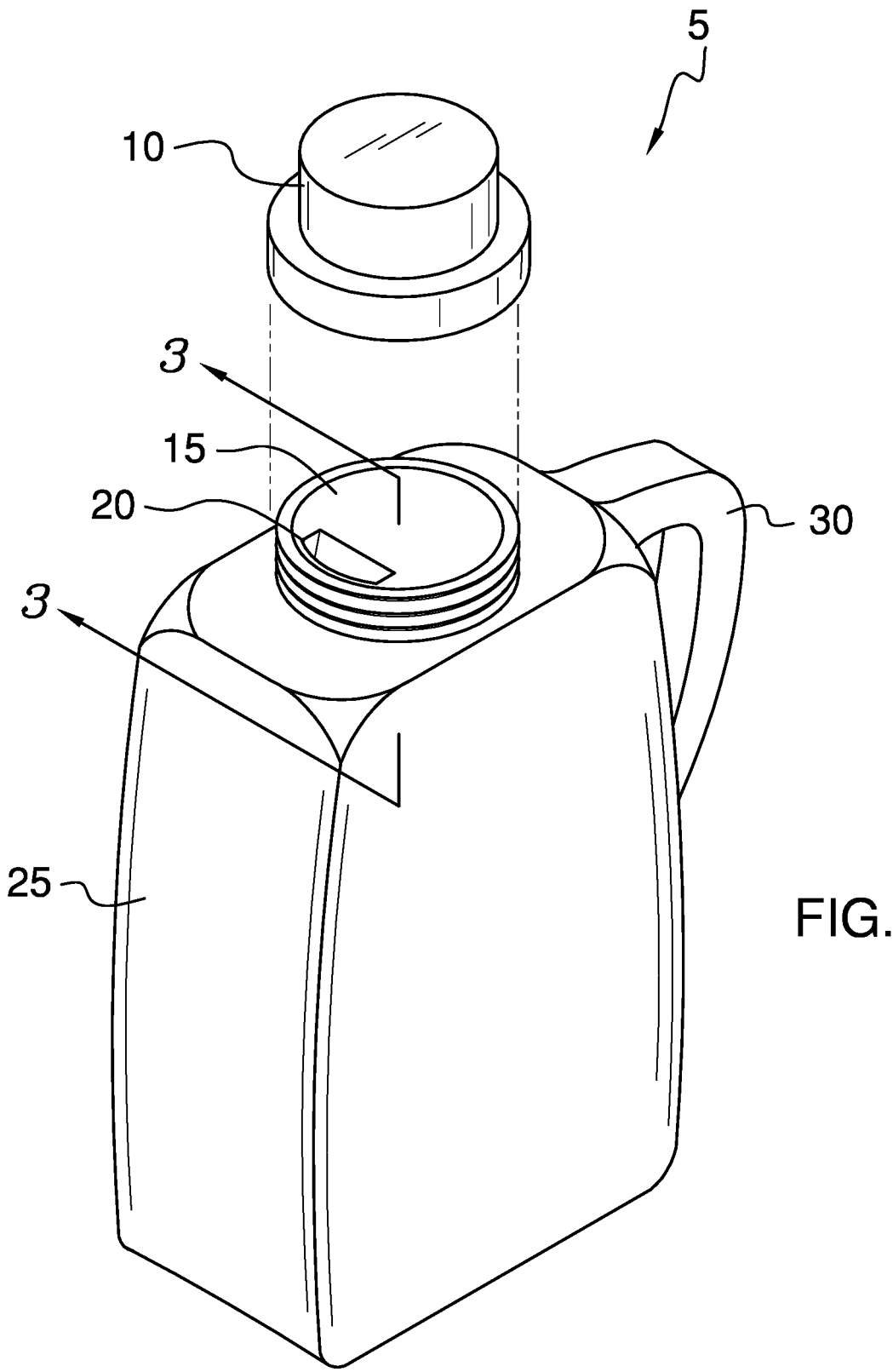
FIG. 1 is an isometric view of the device.
Figure 2:
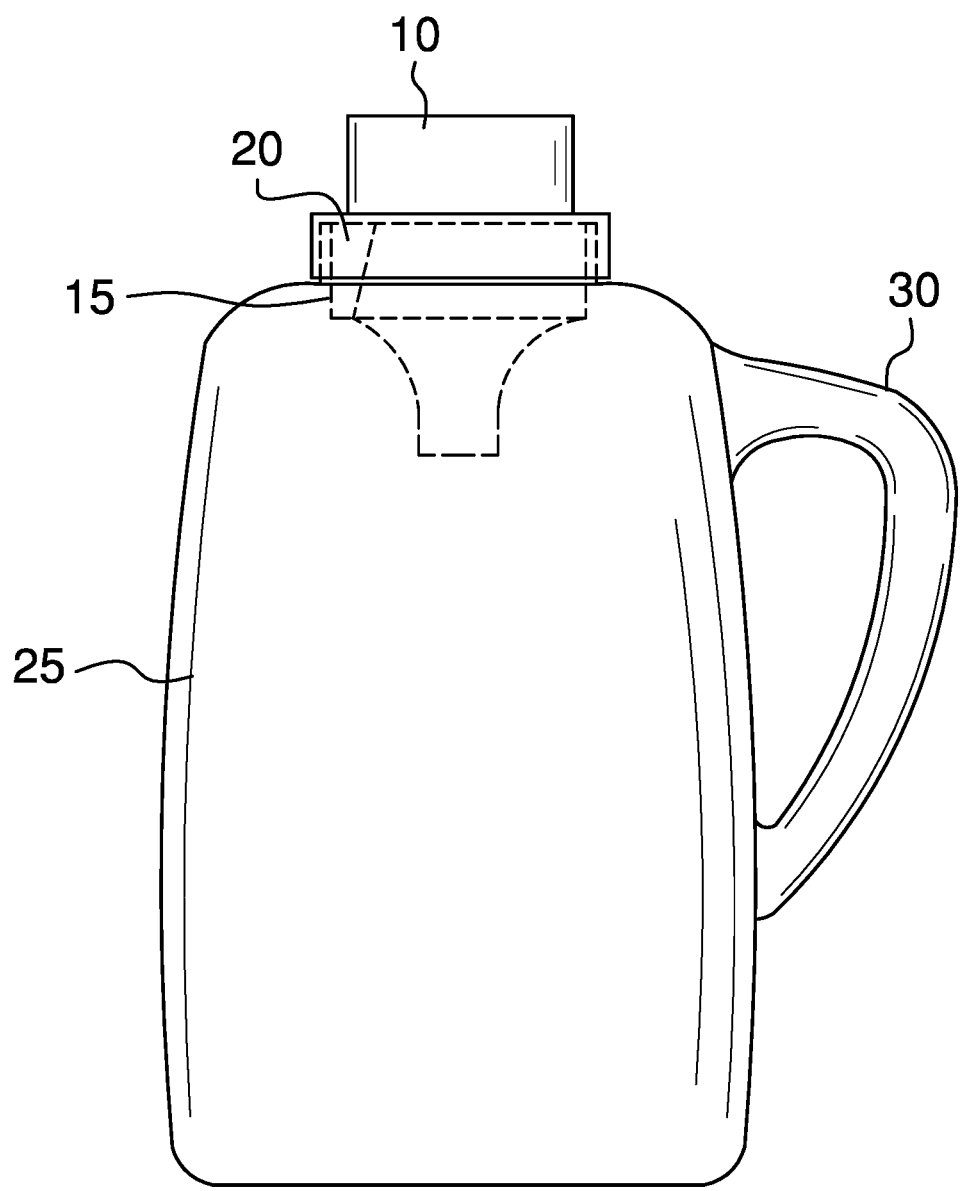
FIG. 2 is a side view of the device showing the insert in dashed lines at the opening of the vessel.
Figure 3:
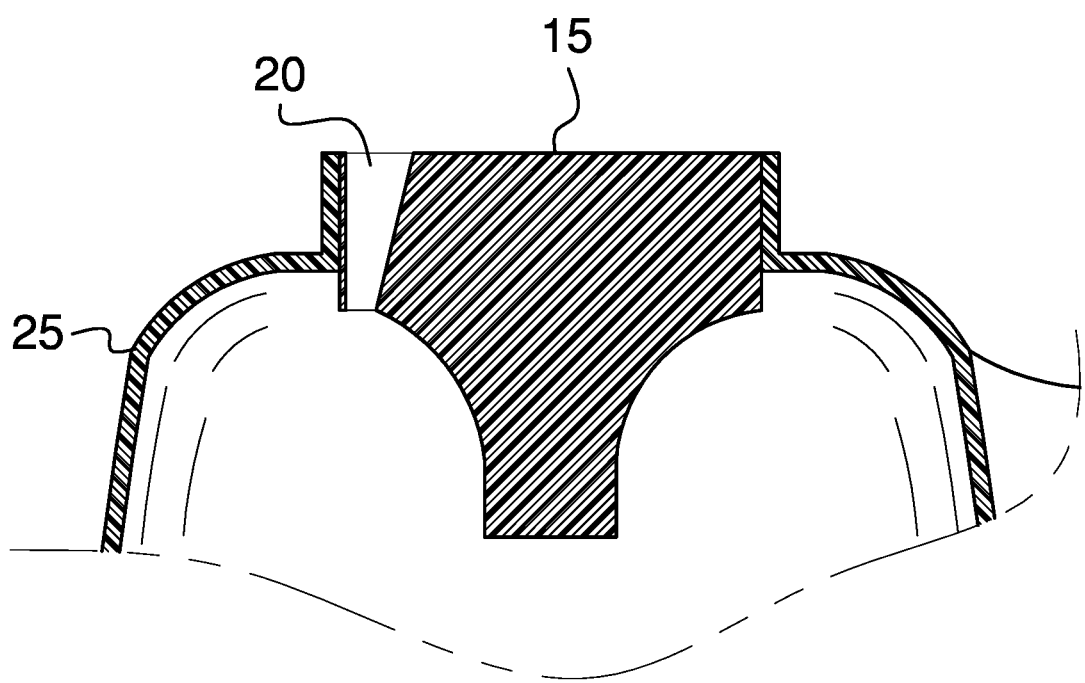
FIG. 3 is a view according to Line 3-3 on FIG. 1.

5—Device
10—Lid
15—Tapered insert
20—Flared opening
25—Container
30..Handle

DETAILED DESCRIPTION OF THE EMBODIMENTS

This device 5 will be used to collect and store urine, particularly on long trips. It will allow the individual to relieve himself or herself without interruption of travel. It will have a tapered insert 15 in the opening of the container 25. The tapered insert can be made as part of the container or be removable. The user will deposit the urine into the container 25 through the tapered insert and then reseal the top using the lid 10 for that purpose. External threads are provided to attach the lid 10 to the container 25.

A flared opening 20 that is formed as part of the tapered insert and located on the side of the insert will be provided. After the urine is deposited into the container, the user will remove the lid 10 and tilt the container 25 so that the urine will flow through the tapered opening 20 on the side of the tapered insert 15. The user would then use the lid to reseal the container. A handle 30 is provided for the convenience of the user.

A deodorizer (not depicted) may be inserted into the container to address the smell issue of stored urine.

Figure 4:
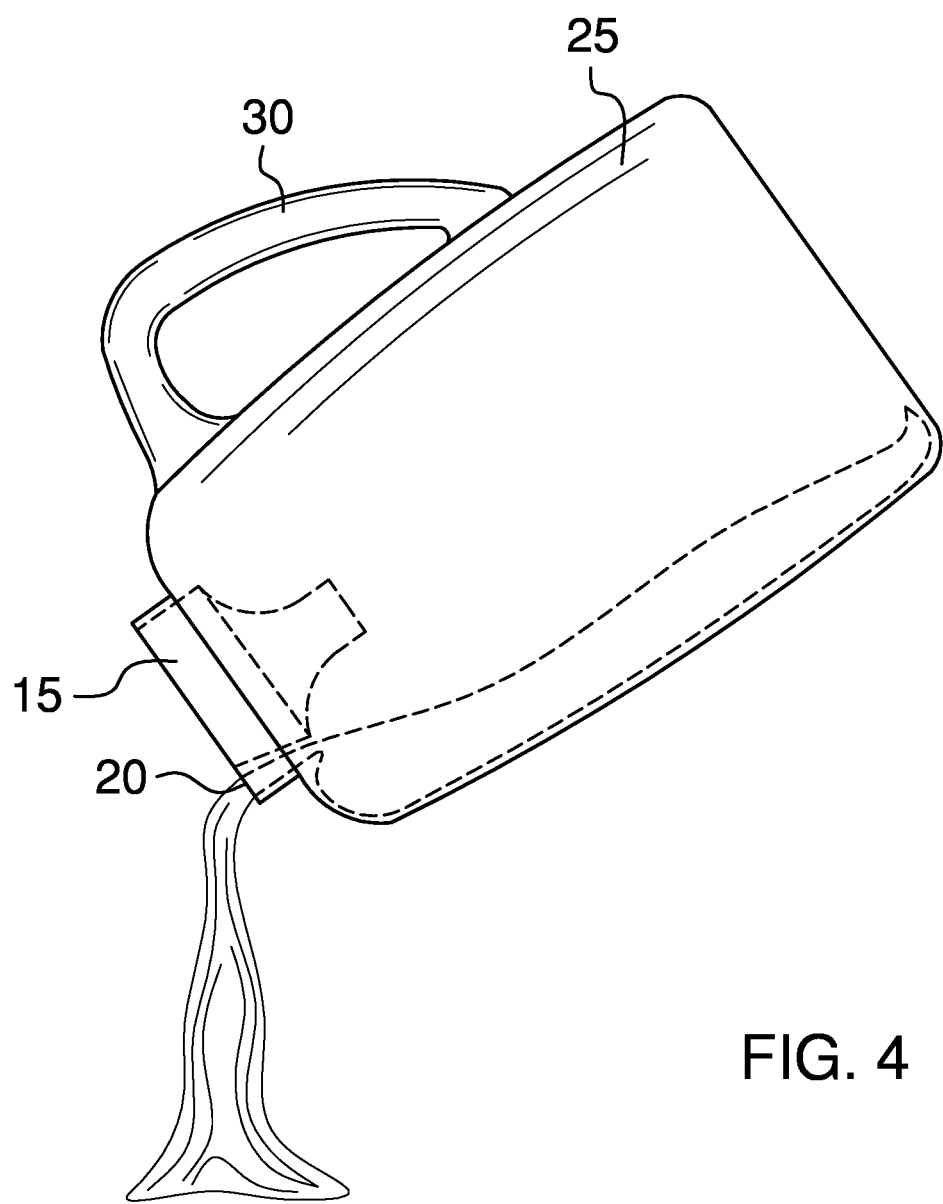
FIG. 4 is a depiction of the device being emptied.

When the device is emptied, the user grabs the handle 30 and tilts the vessel so that the urine flows through the flared opening 20 such as depicted in FIG. 4. Once the contents of the container 25 are emptied the user reattaches the lid 10.

While the embodiments of the invention have been disclosed, certain modifications may be made by those skilled in the art to modify the invention without departing from the spirit of the invention.

The inventor claims:
1. A portable urine container, which is comprised of:
a container;
wherein the container is a predetermined shape;
a handle;
wherein a handle is attached to the container;
a tapered insert;
wherein the tapered insert is provided;
wherein the tapered insert is placed in the opening of the container;
a flared opening;

wherein the flared opening is on the side of the tapered insert;

wherein the flared opening and tapered insert are a single piece;

a lid;

wherein a lid is provided;

wherein the lid is placed over the tapered insert and the flared opening when inserted over the opening of the container.

2. The portable urine container as described in claim 1 wherein a deodorizer is added.

3. The portable urine container as described in claim 1 wherein the flared opening and tapered insert are removable.

4. The portable urine container as described in claim 1 wherein the tapered insert is integral to the container.

* * * * *